United States Patent
Herve

(10) Patent No.: US 8,817,257 B2
(45) Date of Patent: Aug. 26, 2014

(54) METHOD FOR RECONSTRUCTING THE OPTICAL PROPERTIES OF A MEDIUM USING A COMBINATION OF A PLURALITY OF MELLIN-LAPLACE TRANSFORMS OF A MAGNITUDE COMPRISING A TIME DISTRIBUTION OF A RECEIVED SIGNAL, AND ASSOCIATED RECONSTRUCTION SYSTEM

(71) Applicant: Commissariat a l'energie atomique et aux energies alternatives, Paris (FR)

(72) Inventor: Lionel Herve, Corenc (FR)

(73) Assignee: Commissariat à l'energie atomique et aux energies alternatives, Paris (FR)

( * ) Notice: Subject to any disclaimer, the term of this patent is extended or adjusted under 35 U.S.C. 154(b) by 0 days.

(21) Appl. No.: 13/714,807

(22) Filed: Dec. 14, 2012

(65) Prior Publication Data

US 2013/0155407 A1 Jun. 20, 2013

(30) Foreign Application Priority Data

Dec. 16, 2011 (FR) ...................................... 11 61832

(51) Int. Cl.
*G01N 21/59* (2006.01)
*G01N 21/64* (2006.01)
*G06T 11/00* (2006.01)
*G01N 21/47* (2006.01)
*G01N 21/49* (2006.01)
*G01N 21/17* (2006.01)
*A61B 5/00* (2006.01)
*G09B 23/28* (2006.01)

(52) U.S. Cl.
CPC .............. *G01N 21/59* (2013.01); *G06T 11/003* (2013.01); *G01N 2201/0833* (2013.01); *G01N 2021/1787* (2013.01); *A61B 5/4381* (2013.01); *G01N 21/6428* (2013.01); *G09B 23/286* (2013.01); *G01N 21/6408* (2013.01); *A61B 5/0073* (2013.01); *A61B 5/0071* (2013.01); *A61B 5/4312* (2013.01); *G01N 21/64* (2013.01); *G01N 21/4795* (2013.01); *A61B 5/4255* (2013.01); *G01N 2021/6484* (2013.01); *G01N 2201/0826* (2013.01); *A61B 5/4064* (2013.01); *G01N 2201/0697* (2013.01); *G01N 21/6456* (2013.01); *A61B 5/7253* (2013.01); *G01N 21/49* (2013.01); *G01N 2021/6413* (2013.01)
USPC ...................... 356/432; 250/458.1; 250/459.1

(58) Field of Classification Search
USPC ..................... 356/432–440; 250/459.1, 458.1
See application file for complete search history.

(56) References Cited

U.S. PATENT DOCUMENTS

| | | | | |
|---|---|---|---|---|
| 7,675,044 | B2 * | 3/2010 | Laidevant et al. | 250/458.1 |
| 7,977,650 | B2 * | 7/2011 | Laidevant et al. | 250/458.1 |
| 8,263,947 | B2 * | 9/2012 | Da Silva et al. | 250/459.1 |
| 2007/0211253 | A1 * | 9/2007 | Ozcan et al. | 356/432 |
| 2008/0067420 | A1 | 3/2008 | Laidevant et al. | |
| 2008/0260647 | A1 | 10/2008 | Intes et al. | |
| 2010/0224797 | A1 | 9/2010 | Laidevant et al. | |
| 2013/0158926 | A1 * | 6/2013 | Herve | 702/85 |
| 2013/0162793 | A1 * | 6/2013 | Dinten et al. | 348/77 |

(Continued)

FOREIGN PATENT DOCUMENTS

EP 1884765 A1 2/2008

OTHER PUBLICATIONS

Nicolas Ducros et al: "A comprehensive study of the use of temporal moments in time-resolved diffuse optical tomography: part II Three-dimensional reconstructions; Reconstructions from moments in time-resolved diffuse optical tomography", Physics in Medicine and Biology, Taylor and Francis Ltd. London, GB, vol. 54, No. 23, Dec. 7, 2009, pp. 7107-7119, XP020167032, ISSN: 0031-9155.

Arridge S R: "Optical tomography in medical imaging", Inverse problems, Institute of Physics Publishing, Bristol, GB, No. 15, Jan. 1, 1999, pp. R41-R93, XP002404811, ISSN: 0266-5611.

Puszka A et al: "Time-Resolved Reflectance DOT: Experimental Results for Imaging Absorption Contrast in Depth", Biomedical Optics (Biomed) 2012 Paper: BWIA.2, 2012, XP002676624.
French Search Report and Written Opinion, dated May 25, 2012, which issued during the prosecution of French Patent Application No. 1161832.

* cited by examiner

*Primary Examiner* — Hoa Pham
(74) *Attorney, Agent, or Firm* — Troutman Sanders LLP

(57) ABSTRACT

A method reconstructing the optical properties of a medium using a reconstruction system has a radiation source lighting the medium and a detector receiving a signal transmitted by the medium. The steps include lighting the medium using a radiation source, receiving by the detector of a signal emitted by the medium, and processing, for a source-detector pair, of a first distribution of the signal received by the corresponding detector. Then computing the Mellin-Laplace transform, for a given order and a given variable, of a magnitude comprising the first distribution, the order being an integer, the variable being a real number, and reconstructing optical properties of the medium using the Mellin-Laplace transform of said magnitude. The computation step includes computing a plurality of Mellin-Laplace transforms of the magnitude for distinct values of the order, and the reconstruction step is carried out from a combination of the plurality of Mellin-Laplace transforms.

15 Claims, 5 Drawing Sheets

METHOD FOR RECONSTRUCTING THE OPTICAL PROPERTIES OF A MEDIUM USING A COMBINATION OF A PLURALITY OF MELLIN-LAPLACE TRANSFORMS OF A MAGNITUDE COMPRISING A TIME DISTRIBUTION OF A RECEIVED SIGNAL, AND ASSOCIATED RECONSTRUCTION SYSTEM

CROSS-REFERENCE TO RELATED APPLICATION

This application claims priority to French Patent Application No. 11 61832 filed Dec. 16, 2011. The entirety of the priority application is incorporated herein by reference.

FIELD OF THE INVENTION

The present invention relates to a method for reconstructing the optical properties of a medium using a reconstruction system having at least one radiation source capable of lighting a medium and at least one detector capable of receiving a signal transmitted by the medium.

BACKGROUND

The article "*Optical tomography in medical imaging*" by S. R. Arridge, published in the journal "Inverse Problems" in 1999, is known, citing the possible use of the Mellin-Laplace transform of order n for applications to optical tomography.

However, this article does not specifically outline how this transform can be used in the context of the reconstruction of the optical properties of a diffusing medium, with the advantages described below.

The aim of the invention is therefore to propose a method for reconstructing the optical properties of the medium as well as a reconstruction system advantageously using the Mellin-Laplace transform, in particular allowing access to optical diffusion properties that are usually difficult to establish, and for example the spatial distribution of the absorption or diffusion coefficients of a medium.

SUMMARY

To that end, the invention relates to a reconstruction method of the aforementioned type, wherein the computation step includes computing a plurality of Mellin-Laplace transforms of said magnitude for distinct values of the order, and in that the reconstruction step is carried out from a combination of the plurality of Mellin-Laplace transforms.

Reconstruction of the optical properties for example refers to:
- the reconstruction of the absorption properties, the latter in particular being characterized by the absorption coefficient, denoted $\mu_a$,
- the reconstruction of the diffusion properties, the latter in particular being characterized by the reduced diffusion coefficient $\mu'_s$ or the diffusion coefficient D, and
- the reconstruction of the fluorescence properties, the latter in particular being characterized by a response function (F) of a fluorophore, or by a concentration c of a fluorophore, or by another magnitude altogether expressing a quantity q of a fluorophore, the latter for example being endogenous or exogenous.

According to other advantageous aspects of the invention, the reconstruction method includes one or more of the following features, considered alone or according to all technically possible combinations:

- the computation step comprises the computation of at least one Mellin-Laplace transform of said magnitude for an order value greater than or equal to 5, preferably greater than or equal to 8,
- the computation step comprises the computation of $n_{max}+1$ Mellin-Laplace transforms, the order successively taking all values comprised between 0 and $n_{max}$, $n_{max}$ being greater than or equal to 5, preferably greater than or equal to 8,
- the value of the variable is between $1\,\text{ns}^{-1}$ and $20\,\text{ns}^{-1}$,
- the method also includes:
  - the determination, for at least one source-detector pair, of a first modeling function of a diffusion signal of the light between the source and the detector in the medium,
  - the processing, for said at least one source-detector pair, of a second distribution of the signal received by the detector for a reference medium, the received signal being transmitted by the reference medium following the lighting of said medium by the source, and
  - the determination, for said at least one source-detector pair, of a second modeling function of a diffusion signal of the light between the source and the detector in the reference medium,
  - and said magnitude depends on the first distribution, the first modeling function, the second distribution, and the second modeling function,
- said magnitude is obtained by subtracting the product of the second distribution and the first modeling function from the product of the first distribution and the second modeling function,
- said magnitude is the ratio between the product of the first distribution and the second modeling function and the product of the second distribution and the first modeling function,
- the or each radiation source comprises a pulsed light source,
- the or each detector is a time-resolved detector, and
- the optical properties include at least one element from amongst the group of:
  - the light absorption properties, in particular characterized by the absorption coefficient,
  - the diffusion properties, in particular characterized by the reduced diffusion coefficient or the diffusion coefficient, and
  - the fluorescence properties, in particular characterized by a response function of a fluorophore, or by a concentration of the fluorophore, or by a magnitude depending on the quantity of the fluorophore.

The invention also relates to a reconstruction system including
- at least one radiation source capable of lighting the medium,
- at least one detector capable of receiving a signal transmitted by the medium,
- means for processing a distribution of the signal received by the corresponding detector for at least one source-detector pair,
- means for computing the Mellin-Laplace transform, for a given order and a given variable, of a magnitude having the distribution, the order being an integer, the variable being a real number, and
- means for reconstructing the optical properties of the medium using the Mellin-Laplace transform of said magnitude, wherein the computation means are capable of computing the plurality of Mellin-Laplace transforms of said magnitude for distinct values of the order, and in that the reconstruction means are capable of reconstructing the optical properties of the medium from a combination of the plurality of Mellin-Laplace transforms.

According to another advantageous feature of the invention, the reconstruction system also includes computation means capable of computing at least one Mellin-Laplace transform of said magnitude for an order value greater than or equal to 5, preferably greater than or equal to 8.

BRIEF DESCRIPTION OF THE DRAWINGS

These features and advantages of the invention will appear upon reading the following description, provided solely as an example, and done in reference to the appended drawings, in which.

DETAILED DESCRIPTION

Figure 1:
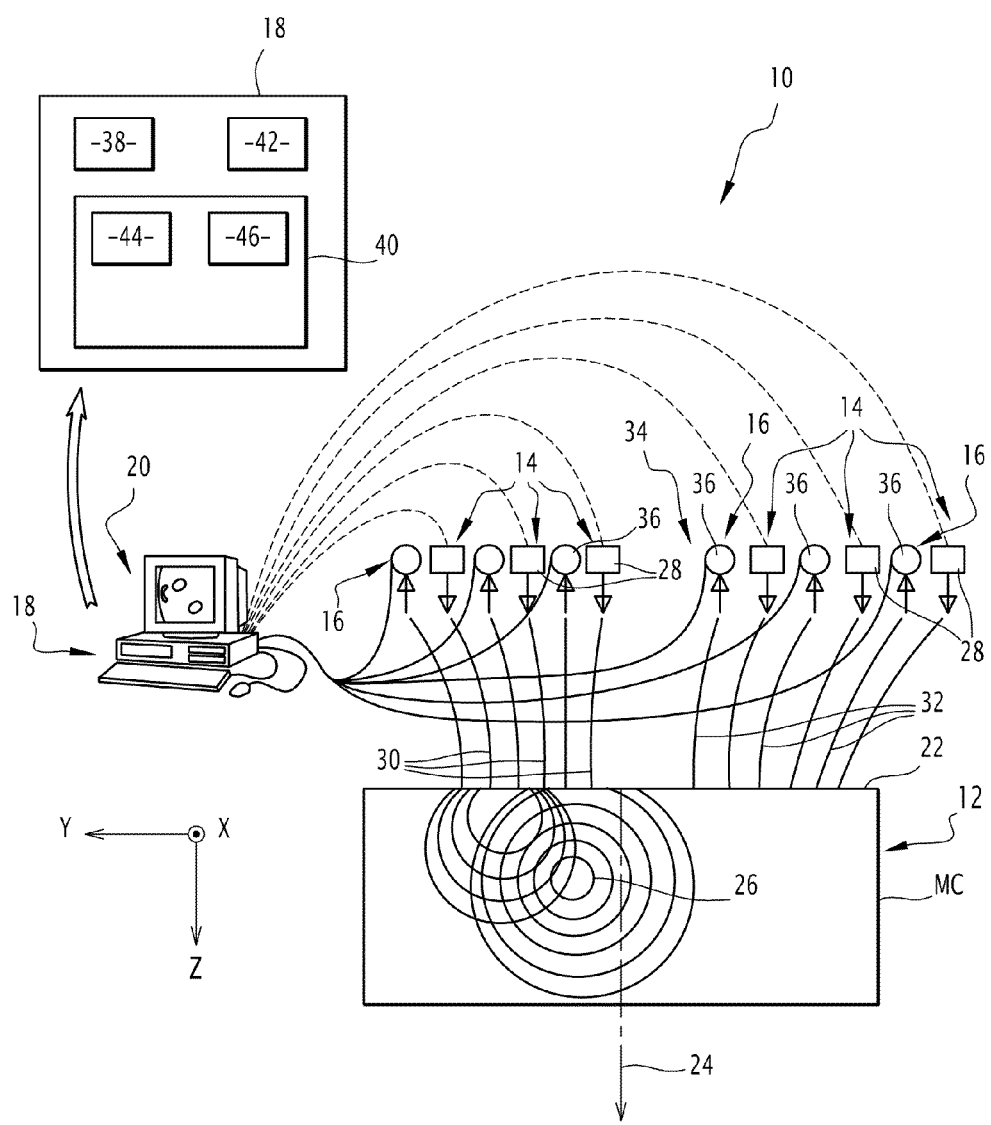
FIG. 1 is a diagrammatic illustration of a reconstruction system according to an example of the invention, capable of reconstructing an image of a medium.

FIG. 1 shows a reconstruction system 10 designed to examine a medium 12 by acquiring an image of the medium 12, then processing that image.

The reconstruction system 10 includes a plurality of radiation sources 14 for lighting the medium 12 and a plurality of detectors 16 for receiving a signal transmitted by the medium 12. These radiation sources 14 and the detector 16 are for example arranged in a probe, not shown.

The system 10 includes an information processing unit 18 and a screen 20 for displaying an image of the medium.

In the described embodiment, the system 10 is a time system, and each radiation source 14 is a pulsed radiation source. Each detector 16 is a time-resolved detector, i.e. a detector making it possible to measure the time distribution of the arrival time of the photons, also called TCSPC (Time-Correlated Single Photon Counting).

According to the illustrated example, the medium 12 has an observation surface 22, in the form of a plane parallel to a longitudinal axis X and a transverse axis Y, and in contact with which the sources 14 and the detectors 16 can be applied. The medium 12 has an observation direction 24 extending along a vertical axis Z and substantially perpendicular to the observation surface 22.

In the example embodiment of FIG. 1, the medium 12 is a medium to be characterized, denoted MC and visible in FIG. 1. The medium to be characterized MC comprises animal or human biological tissue. The medium to be characterized MC is for example an area of an organ such as the brain, a breast, the prostate, the digestive tube, or other organs in which fluorophores can be injected. More generally, the medium to be characterized MC is a biological medium, for example an organ, for which one wishes to determine the optical diffusion properties, and in particular the spatial distribution of coefficients such as the absorption coefficient or the diffusion coefficient.

The medium to be characterized MC is a diffusing medium containing inclusions having different optical absorption or diffusion properties from those of the medium. A single inclusion 26 is shown in FIG. 1 for clarity of the drawing.

Each pulsed radiation source 14 comprises a pulsed light source 28 and an optical excitation fiber 30 connected to the pulsed source 28 for transmission of the light pulse to the medium 12. When such a fibrous source is used, the free end of the excitation fiber 30 is assimilated with the source s.

In one alternative not shown, each pulsed radiation source 14 comprises an optical excitation fiber 30 connected to a single pulsed light source shared by the plurality of radiation sources 14. According to this alternative, the system 10 also includes an optical switch or a multiplexer to select the excitation fiber 30 in which the light beam is sent.

Also alternatively, the set of pulsed radiation sources 14 is made up of a single pulsed light source and a mirror device of the MEMS (MicroElectroMechanical Systems) type, not shown, to scan the medium 12 with the light coming from the pulsed light source. Also alternatively, the source 14 is a multiplexed source, delivering light pulses with different wavelengths.

In the case of an examination of the surface 22 of the medium or a shallow examination of the medium 12, i.e. a depth of several millimeters to several centimeters, the wavelength of each pulsed radiation source 14 is preferably in the visible or near infrared region, i.e. between 500 nm and 1300 nm. The repetition rate is approximately 50 MHz, and in general between 10 MHz and 100 MHz.

The pulses transmitted by each pulsed radiation source 14 have a length between 10 picoseconds and 1 nanosecond, preferably between 10 picoseconds and 100 picoseconds, each pulsed light source 28 being able to generate a time width pulse lasting between 10 picoseconds and 1 nanosecond, preferably between 10 picoseconds and 100 picoseconds.

Each time-resolved detector 16, also denoted d, comprises an optical detection fiber 32 connected to a time-resolved detection module 34. When such a fibrous detector is used, the free end of the optical detection fiber 32 is assimilated with the detector d.

In the example embodiment of FIG. 1, the detection module 34 comprises a detection member 36 for each detector 16. In one alternative not shown, the detection module 34 comprises a detection member shared by several detectors 16, in particular a single detection member for all of the detectors 16.

The detection member 36 is for example a photomultiplier, an avalanche photodiode (APD), a single-photon avalanche diode (SPAD), or an image intensifier tube with one or more anodes (Multi-Channel Plate).

In this example, the probe is a compact probe for diagnosing certain cancers, such as a portable probe for diagnosing breast cancer, and endorectal probe for diagnosing prostate cancer, or a dermatological probe. Alternatively, the probe is an endoscopic probe such as a flexible probe for diagnosing digestive cancer. Alternatively, the probe is a device applicable to other organs.

The information processing unit 18 comprises a data processor 38 and a memory 40 associated with the processor 38.

The processing unit 18 comprises means 42 for processing, from at least one source 14-detector 16 pair, a first distribution $B_{sd}$ of a signal received by the corresponding detector 16 for the medium to be characterized MC, the received signal being transmitted by the diffusing medium to be characterized MC following the lighting of said medium MC by the corresponding source 14. The corresponding source 14 and detector 16, respectively, are referenced by indices s and d, respectively.

In the described embodiment, the first distribution is a time distribution respectively denoted $B_{sd}(t)$. The processing means 42 are preferably made in the form of one or more electronic boards connected to the detector 16 and making it possible to measure the time distribution of the arrival time of the photons.

Each pulsed light source 28 comprises a pulsed laser. Alternatively, each pulsed light source 28 comprises a laser diode. Also alternatively, each pulsed light source 28 comprises a constant light source whereof the light intensity is modulated into pulses of equivalent length by a rapid-closing device. In this way, the source can transmit a ray of light assuming the form of a time pulse.

According to this particular embodiment, the end of each excitation fiber 30 extends perpendicular to the observation surface 22, i.e. along the axis Z, or obliquely relative to the axis Z, so as to emit light that is slanted relative to the observation surface 22.

The memory 40 is capable of storing software 44 for computing a plurality of Mellin-Laplace transforms $Y_{sd}^{(p,n)}$, for a variable p, also called width, and distinct given values of an order n, a magnitude $Y_{sd}(t)$ comprising the first distribution $B_{sd}(t)$, the order n being an integer and the variable p being a real number.

The Mellin-Laplace transform of order n and width p of a function f is denoted $f^{(p,n)}$, and verifies the following equation:

$$f^{(p,n)} = \frac{1}{n!} \int_0^{+\infty} (pt)^n \cdot \exp(-pt) \cdot f(t) \cdot dt \qquad (1)$$

where $1/n!$ represents a normalization term.
The Mellin-Laplace transform $f^{(p,n)}$ of the function f is also written:

$$f^{(p,n)} = \int_{-\infty}^{+\infty} W^{(p,n)} \cdot f(t) \cdot dt \qquad (2)$$

where $W^{(p,n)}$ represents a time window defined by the following equation:

$$W^{(p,n)} = \frac{H(t) \cdot (pt)^n \cdot \exp(-pt)}{n!} \qquad (3)$$

with H(t) representing the known Heaviside function.

Figure 2:
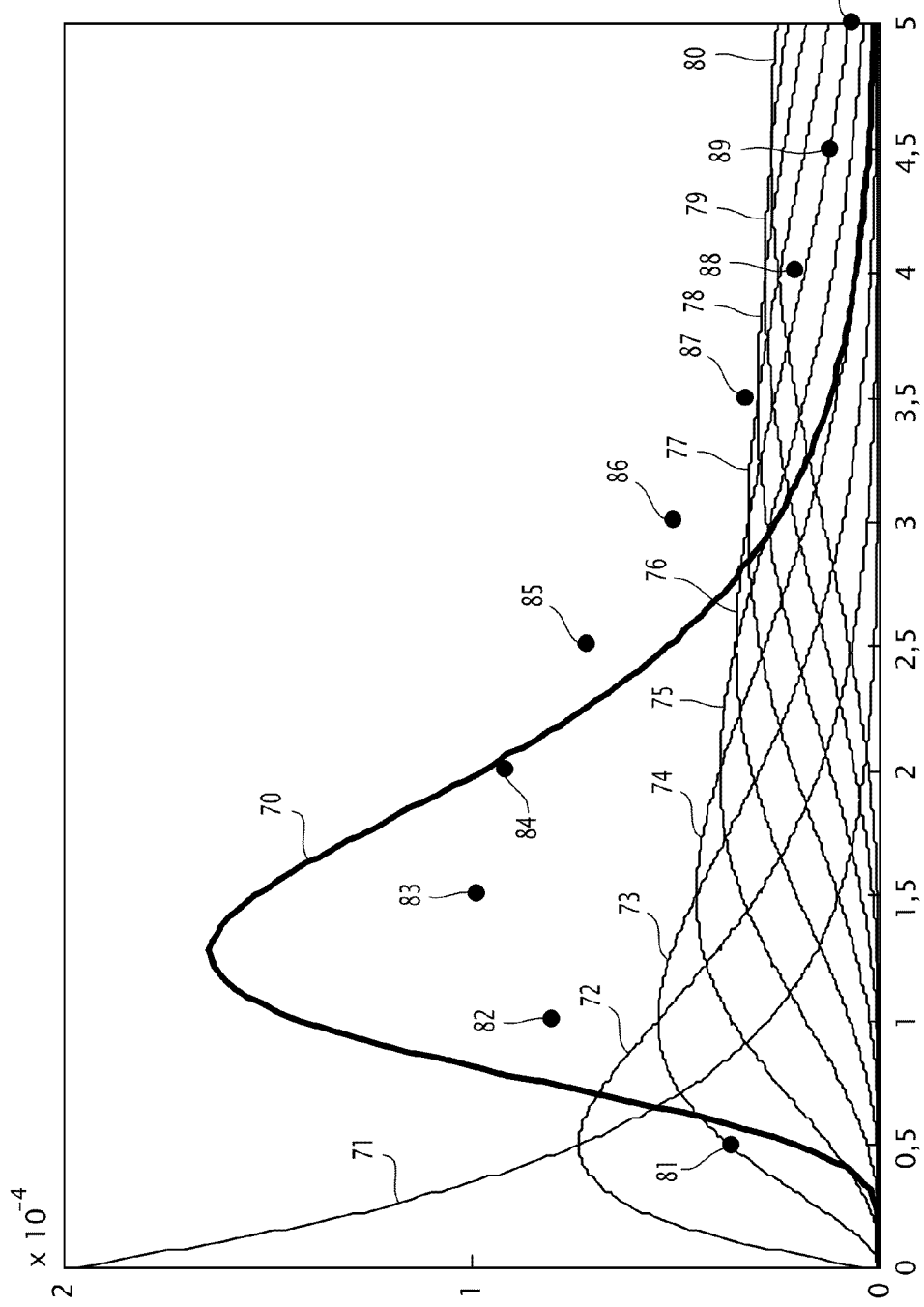
FIG. 2 is a set of curves showing a time distribution of the signal received by the system of FIG. 1 and the Mellin-Laplace transforms of that time distribution computed for order values between 0 and 9.

In FIG. 2, the function f is represented by the curve 70 in bold lines, and the time windows $W^{(p,n)}$ are represented by curves 71 to 80, with p equal to 2 $ns^{-1}$ and with the order n respectively taking the successive integer values between 0 and $n_{max}$, with $n_{max}$ equal to 9. The positions $((n+1)/p, pf^{(p,n)})$ are referenced by points 81 to 90, for the same values of the width p and the order n. The area of the time windows $W^{(p,n)}$ is equal to $1/p$, and the average position of said time windows $W^{(p,n)}$ is equal to $(n+1)/p$.

In general, the Mellin-Laplace transform $f^{(p,n)}$ of order n and width p of the function f can be considered like any function including the term $$\int_0^{+\infty} (pt)^n \cdot \exp(-pt) \cdot f(t) \cdot dt$$

to within a multiplicative coefficient.

In the described embodiment, at least one Mellin-Laplace transform $Y_{sd}^{(p,n)}$ is computed for a value of order n greater than or equal to 5, preferably greater than or equal to 8.

In the described embodiment, the order n assumes a value between 0 and a maximum value $n_{max}$. The order n for example successively assumes all values between 0 and $n_{max}$. In other words, $n_{max}+1$ Mellin-Laplace transforms $Y_{sd}^{(p,n)}$ are then computed for the computation software 44. The maximum value $n_{max}$ is greater than or equal to 5, preferably greater than or equal to 8.

The combination of Laplace transforms of different orders, and in particular small orders, i.e. n close to 0, with large orders, i.e. $n \geq 5$, makes it possible to account for the contribution to the detected signal of photons emitted at moments very shortly after the excitation pulse (small orders) as well as more distant moments (large orders), the latter being called delayed photons, as they are detected several nanoseconds after the excitation light pulse.

The described embodiment, the value of the width p is between 1 $ns^{-1}$ and 20 $ns^{-1}$, where ns is the abbreviation of nanosecond.

The memory 40 is also capable of storing software 46 for reconstructing optical properties of the medium 12 from a combination of the plurality of Mellin-Laplace transforms $Y_{sd}^{(p,n)}$ of said magnitude $Y_{sd}(t)$. The reconstruction software 46 is capable of reconstructing optical coefficients, such as the optical absorption coefficient $\mu_a$ or the diffusion coefficient D, from the spatial distribution. Alternatively, the reconstruction software 46 can reconstruct a fluorescence map of the medium 12.

In the described embodiment, the magnitude $Y_{sd}(t)$ is a corrected signal making it possible to account for the instrument response, also called corrective distribution, and is described in more detail hereafter.

Alternatively, the magnitude on which the plurality of Mellin-Laplace transforms is computed is the first distribution $B_{sd}(t)$.

Alternatively, the computation means 44 and the reconstruction means 46 are made in the form of programmable logic components or dedicated integrated circuits.

Figure 3:
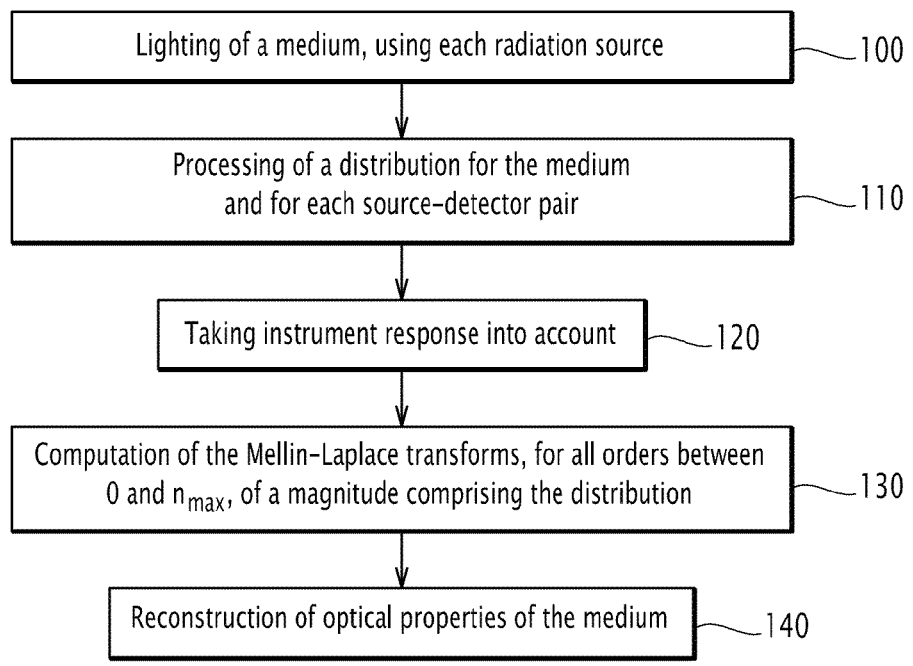
FIG. 3 is a flowchart of a reconstruction method according to an example of the invention.

The operation of the imaging system 10 according to the invention is described hereafter using FIG. 3, which shows a flowchart of the image processing method according to the invention.

During step 100, the medium to be characterized MC is lit by the corresponding source(s) 14. In the event of a plurality of sources 14, the lighting of the medium 12 is done successively for each of the sources 14. When it is lit, the medium to be characterized MC transmits an optical diffusion signal in return, which may be detected by the or each detector 16, and the first distribution of the received signal $B_{sd}(t)$ is processed, during step 110, for each source 14-detector 16 pair, also denoted (s, d), using the processing means 42.

The first time distribution $B_{sd}(t)$ verifies the following equation:

$$B_{sd}(t) = IRF_{sd}(t) * G_{sd}(t) \qquad (4)$$

where $IRF_{sd}(t)$ represents the instrument response, i.e. the influence of the source s and the detector d on the first processed distribution, and $G_{sd}(t)$ represents a first modeling function of a diffusion signal of a light between the source 14 and the detector 16 in the medium to be characterized MC.

$S_s(t)$ denotes the time response of the source 14, also denoted s. In this example, the source 14 is a brief light pulse, often modeled by a periodic Dirac-type distribution. $S_s(t)$ represents the time intensity of the emitted signal. When the source 14 is fibrous (light source coupled to an optical fiber), it is the end of the optical excitation fiber 30 that is then considered the source, as previously indicated.

$D_d(t)$ denotes the time response of the detector 16, also denoted d. This response in particular indicates the amount of time between the arrival of a photon on the detector 16 and the detection of that photon. When the detector 16 is fibrous (detector coupled to an optical fiber), the end of the detection fiber 32 is considered the detector, as previously indicated.

The instrument response, denoted $IRF_{sd}(t)$, is generally estimated, the index sd corresponding to an excitation source s and detector d pair. This instrument response is obtained by combining Ss(t) and Dd(t) as follows: $IRF_{sd}(t)=S_s(t)*D_d(t)$, where * designates the convolution integral.

When one has several sources and several detectors, $IRF_{sd}(t)$ is determined for each source-detector pair, as each source and each detector has its own response. In practice, this is done by placing a source (or an optical fiber end making up the source) across from the detector (or an optical fiber end making up the detector). This assumes careful alignment between the source and the detector, and takes time, in particular when the number of sources and detectors is increased. As an example, when there are 10 sources and 10 detectors, 100 instrument response functions $IRF_{sd}$ must be determined.

During step 120, the instrument response $IRF_{sd}(t)$ is taken into account using a second time distribution $A_{sd}(t)$ and a second modeling function $G_{sd}^0(t)$. The second time distribution $A_{sd}(t)$ is processed for a reference medium MR and under the same experimental conditions as for the first time distribution $B_{sd}(t)$.

The reference medium MR, also called ghost, is known in itself and is, for example, described in document FR 2 950 241 A1. The ghost MR has known optical characteristics. The ghost MR is, for example, a ghost having absorption $\mu_a^0$ and diffusion $D^0$ coefficients with median values for human tissues, for example equal to 0.2 cm$^{-1}$ and 10 cm$^{-1}$, respectively.

The processing of the second time distribution $A_{sd}(t)$ is preferably done in a preliminary manner, before step 100, and the reference medium MR is then replaced by the medium to be characterized MC at the beginning of step 100.

Alternatively, the processing of the second time distribution $A_{sd}(t)$ is done during step 120, which requires changing the medium 12, and replacing the medium to be characterized MC with the reference medium MR.

The second time distribution $A_{sd}(t)$ then verifies the following equation:

$$A_{sd}(t)=IRF_{sd}(t)*G_{sd}^0(t) \quad (5)$$

The first and second modeling functions $G_{sd}(t)$, $G_{sd}^0(t)$ are for example Green functions, well known in the optical diffusion field. Each Green function $G_{sd}(t)$, $G_{sd}^0(t)$ represents the density of photons at the detector 16 when the medium 12, i.e. the reference medium MR for the first modeling function and the medium to be characterized MC for the second modeling function, respectively, is lit by the source 14, where s and d are the indices respectively designating the source 14 and the detector 16.

The corrected signal $Y_{sd}(t)$ is then computed as a function of the first distribution $B_{sd}(t)$, the first modeling function $G_{sd}(t)$, the second distribution $A_{sd}(t)$ and the second modeling function $G_{sd}^0(t)$.

The corrected signal $Y_{sd}(t)$ is the result of a comparison operation of the product of the second distribution $A_{sd}$ and the first modeling function $G_{sd}$ with the product of the first distribution $B_{sd}$ and the second modeling function $G_{sd}^0$. The comparison operation comprises an arithmetic operation of the product of the second distribution $A_{sd}$ and the first modeling function $G_{sd}$ with the product of the first distribution $B_{sd}$ and the second modeling function $G_{sd}^0$.

The arithmetic operation is, for example, a subtraction of the product of the second distribution $A_{sd}$ and the first modeling function $A_{sd}$ from the product of the first distribution $B_{sd}$ and the second modeling function $G_{sd}^0$.

In the described embodiment, the product of the second distribution $A_{sd}(t)$ and the first modeling function $G_{sd}(t)$ and the product of the first distribution $B_{sd}(t)$ and the second modeling function $G_{sd}^0(t)$ are convolution integers, the first $B_{sd}(t)$ and second $A_{sd}(t)$ distributions being time distributions.

The corrected signal $Y_{sd}(t)$ verifies the following equation:

$$Y_{sd}(t)=B_{sd}(t)*G_{sd}^0(t)-A_{sd}(t)*G_{sd}(t) \quad (6)$$

Alternatively, the arithmetic operation is the ratio between the product of the first time distribution $B_{sd}(t)$ and the second modeling function $G_{sd}^0(t)$ and the product of the second time distribution $A_{sd}(t)$ and the first modeling function $G_{sd}(t)$.

According to this alternative, the corrected signal $Y_{sd}(t)$ then verifies the following equation:

$$Y_{sd}(t) = \frac{B_{sd}(t)*G_{sd}^0(t)}{A_{sd}(t)*G_{sd}(t)} \quad (7)$$

Complementarily, the first modeling function $G_{sd}(t)$ is approximated using the Green function $G_{sd}^1(t)$ for the medium to be characterized MC, and the following equations are then obtained:

$$\begin{aligned} Y_{sd}(t) &= B_{sd}(t)*G_{sd}^0(t) - A_{sd}(t)*G_{sd}^1(t) \quad (8) \\ &= IRF_{sd}(t)*G_{sd}(t)*G_{sd}^0(t) - IRF_{sd}(t)*G_{sd}^0(t)*G_{sd}^1(t) \\ &= IRF_{sd}(t)*G_{sd}^0(t)*(G_{sd}(t)-G_{sd}^1(t)) \\ &= A_{sd}(t)*(G_{sd}(t)-G_{sd}^1(t)) \\ &= -A_{sd}(t)*\left(\int G_s^1(\vec{r},t)*\delta\mu_a(\vec{r},t)*G_d^1(\vec{r},t)d\vec{r} + \int \vec{\nabla} G_s^1(\vec{r},t)*\delta D(\vec{r},t)*\vec{\nabla} G_d^1(\vec{r},t)d\vec{r}\right) \end{aligned}$$

where $\mu_a$ and D respectively represent the absorption coefficient and the diffusion coefficient of the medium to be characterized MC, $IRF_{sd}(t)$ represents the instrument response, $G_s(r,t)=G(r_s,r,t)$ is the Green function representing the density of photons at a location r of the medium MC when the medium MC is lit by the source s situated at $r_s$, $G_d(r,t)=G(r_d,r,t)$ is the Green function representing the density of photons at the location r of the medium MC when the medium to be characterized MC is lit by the source s situated at $r_d$. This is also written $G_d(r,t)=G(r,r_d,t)$. Thus, this Green function also represents the density of photons at the detector ($r_d$) when the medium to be characterized MC is lit by a source situated at r.

In other words, $G_{sd}(t)$ corresponds to the real values $\mu_a(r, t)$ and $D(r, t)$, i.e. the desired values, and $G_{sd}^1(t)$ corresponds to approximate values $\mu^1_a(r, t)$ and $D^1(r, t)$, with $\mu_a(r, t)=\mu^1_a(r, t)+\delta\mu_a(r, t)$ and $D(r, t)=D^1(r, t)+\delta D(r, t)$. The process of reconstructing the optical properties is generally iterative, such that during each iteration, values $\mu^1_a(r)$ and $D^1(r)$ are obtained, to which the Green functions $G_{sd}^1(t)$ correspond for each source-detector pair sd. The aim of the reconstruction method is then to minimize $\delta\mu_a(r, t)$ and $\delta D(r, t)$, which makes it possible to urge $\mu_a^1(r, t)$ and $D^1(r, t)$ toward $\mu_a(r, t)$ and $D(r, t)$, respectively.

The coefficients $\mu_a$ and D are constant over time, and the values $\mu_a(r, t)=\mu_a(r)\partial(t)$ and $D(r,t)=D(r)\partial(t)$, $\partial(t)$ represent a Dirac distribution at moment t.

The computation of the corrected signal $Y_{sd}(t)$, also called corrected time distribution, therefore does away with precise knowledge of the instrument response $IRF_{sd}(t)$ according to equations (6), (7) or (8). This makes it possible to avoid relatively lengthy and tedious experimental measurements in order to determine the instrument response of the imaging system 10.

Alternatively, the instrument response $IRF_{sd}(t)$, representing the time distribution of the pulse generated by the radiation source and detected by the detector in the absence of a diffusive medium, is measured, for each source-detector pair (s, d), during a calibration operation during which the source s is placed across from the detector d in the absence of the medium 12.

During step 130, the Mellin-Laplace transforms $Y_{sd}^{(p,n)}$ of the corrected distribution are then computed for different values of the order n between 0 and $n_{max}$, preferably for all of the successive values between 0 and $n_{max}$, according to the following equation:

$$Y_{sd}^{(p,n)} = \sum_{i+j=n} \left( B_{sd}^{(p,i)} \cdot G_{sd}^{0(p,j)} - A_{sd}^{(p,i)} \cdot G_{sd}^{(p,j)} \right) \quad (9)$$

However, the corrected distribution $Y_{sd}(t)$ verifies the following equation:

$$Y_{sd}(t)=-A_{sd}(t)*(\int G_s^1(\vec{r},t)* \delta\mu_a(\vec{r},t)*G_d^1(\vec{r},t)d\vec{r}+ \int \vec{\nabla}G_s^1(\vec{r},t)*\delta D(\vec{r},t)*\vec{\nabla}G_d^1(\vec{r},t)d\vec{r}) \quad (10)$$

Equations (9) and (10) then make it possible to obtain the following equation, given that the Mellin-Laplace transform of a convolution integer of two terms is equal to the product of the Mellin-Laplace transforms of each of those two terms:

$$Y_{sd}^{(p,n)} = -\sum_{i+j+k=n} A_{sd}^{(p,k)} \cdot \left( \int G_s^{1(p,i)}(\vec{r}) \cdot \delta\mu_a(\vec{r}) \cdot G_d^{1(p,j)}(\vec{r})d\vec{r} + \int \vec{\nabla}G_s^{1(p,i)}(\vec{r}) \cdot \delta D(\vec{r}) \cdot \vec{\nabla}G_d^{1(p,j)}(\vec{r}) \cdot d\vec{r} \right) \quad (11)$$

Equation (11) thus makes it possible to compute the Mellin-Laplace transform of order n of the corrected distribution $Y_{sd}^{(p,n)}$ of the Mellin-Laplace transforms of the second time distribution $A_{sd}(t)$ and Green functions $G_s^1(r)$, $G_d^1(r)$ approximating the first modeling function $G_{sd}(t)$.

The medium 12 is discretized into a plurality M of voxels referenced m, with m being between 1 and M, so as to compute the Mellin-Laplace transforms of the Green functions $G_s^1(r)$, $G_d^1(r)$. The discretized Green functions $G_s^1(r)$, $G_d^1(r)$ for each voxel m are denoted $G_s^1(r_m)$, $G_d^1(r_m)$.

According to one alternative in which the instrument response $IRF_{sd}$ is measured for each source-detector pair (s, d), during a calibration operation, the Mellin-Laplace transforms of the first distribution $B_{sd}^{(p,n)}$ and the instrument response $IRF_{sd}^{(p,n)}$ are computed for different values of the order n between 0 and $n_{max}$, preferably for all of the successive values between 0 and $n_{max}$.

The reconstruction of optical properties of the medium 12 is then done during step 140, so as for example to determine the factors $\vec{\mu}_a$ and $\vec{D}$, the terms $\mu_a(m)$ and $D(m)$ of which, discretized for each voxel m, i.e. $\mu_a(\vec{r}=\vec{r}_m)$ et $D(\vec{r}=\vec{r}_m)$, constitute the maps of the desired optical properties.

The reconstruction step then aims to resolve the following matrix system:

$$\underline{Y}=\underline{W}\underline{X}, \quad (12)$$

where $\underline{Y}$ represents an observation vector, $\underline{W}$ represents a transition matrix, and $\underline{X}$ represents a vector of the unknowns.

The observation vector $\underline{Y}$ contains the Nn Mellin-Laplace transforms for the corrected distribution $Y_{sd}^{(p,n)}$, with Nn equal to $n_{max}+1$, computed for all of the successive values of the order n between 0 and $n_{max}$ and for the considered source-detector (s, d) pairs.

For each triplet (s, d, n) of the indices s, d and the order n, an index I is defined as follows:

$$I=(s-1)\times Nd\times Nn+(d-1)\times Nn+n \quad (13)$$

where Nd is the number of considered detectors 16.

The maximum value of the index I is equal to Imax, such that:

$$I_{max}=Ns\times Nd\times Nn \quad (14)$$

The observation vector $\underline{Y}$ then comprises Imax lines.

The passage matrix $\underline{W}$ includes a first portion $W^\mu$ comprising first terms denoted $W^\mu(I,m)$ and a second portion $W^D$ comprising second terms denoted $W^D(I,m)$. This matrix is called the sensitivity matrix of the measurements Y to the optical properties X.

The first terms $W^\mu(I,m)$ verify the following equation:

$$W^\mu(I, m) = -\sum_{i+j+k=n} A_{sd}^{(p,k)} \cdot G_s^{1(p,i)}(\vec{r}_m) \cdot G_d^{1(p,j)}(\vec{r}_m) \cdot V_m \quad (15)$$

and the second terms $W^D(I,m)$ verify the following equation:

$$W^D(I, m) = -\sum_{i+j+k=n} A_{sd}^{(p,k)} \cdot \vec{\nabla}G_s^{1(p,i)}(\vec{r}_m) \cdot \vec{\nabla}G_d^{1(p,j)}(\vec{r}_m) \cdot V_m \quad (16)$$

where $V_m$ represents a volume element surrounding the mesh m, such as the volume of the Voronoi cell. In other words, $V_m$ represents the volume of the voxel m.

According to this embodiment, during each iteration, the Mellin-Laplace transforms, of various orders, of $G_s^1(t)$ and $G_d^1(t)$ are determined, in particular using the following expression:

$$-\nabla D(\vec{r})\nabla G_s^{1(p,n)}(\vec{r}) + \left(\mu_a(\vec{r}) + \frac{p}{c}\right)G_s^{1(p,n)}(\vec{r}) = \quad (17)$$

$$\begin{cases} \delta(r) & \text{if } n = 0 \\ \frac{p}{c}G_s^{1(p,n-1)}(\vec{r}) & \text{if } n > 0 \end{cases}$$

Thus, during each iteration, $G_s^{1(p,n=0)}$ is determined, then the transforms of higher order are determined iteratively, using the above expression when n>0. During the first iteration, $D=D^0$ and $\mu_a=\mu_a^0$ are used, and during subsequent iterations, $D=D^1$ and $\mu_a=\mu_a^1$ are used. The same reasoning naturally applies to determine the Mellin-Laplace transforms of the function $G_d^1(t)$.

The transition matrix $\underline{W}$ then comprises Imax lines and 2M columns.

Each term $W^\mu(I,m)$, $W^D(I,m)$ of the transition matrix $\underline{W}$ is determined by modeling, upon each iteration, as a function of the optical properties determined during the preceding iteration, or during the first iteration, as a function of optical properties initialized by the operator. This initialization is done for example considering a homogenous medium 12.

The vector of the unknowns $\underline{X}$ comprises 2M lines and one column, and contains the unknowns $\mu_a(m)$ and $D(m)$ for each of the M voxels. The first M lines correspond to the unknowns $\mu_a(m)$ and the following M lines of the vector $\underline{X}$ correspond to the unknowns $D(m)$.

The inversion of the transition matrix $\underline{W}$ is done using inversion algorithms well known by those skilled in the art, such as a gradient descent algorithm, an algebraic reconstruction technique (ART), a singular value decomposition (SVD), or a conjugated gradients method. The process stops when a convergence criterion has been met, for example when the distance between two successive vectors $\underline{X}$ is below a predetermined threshold.

Figure 4:
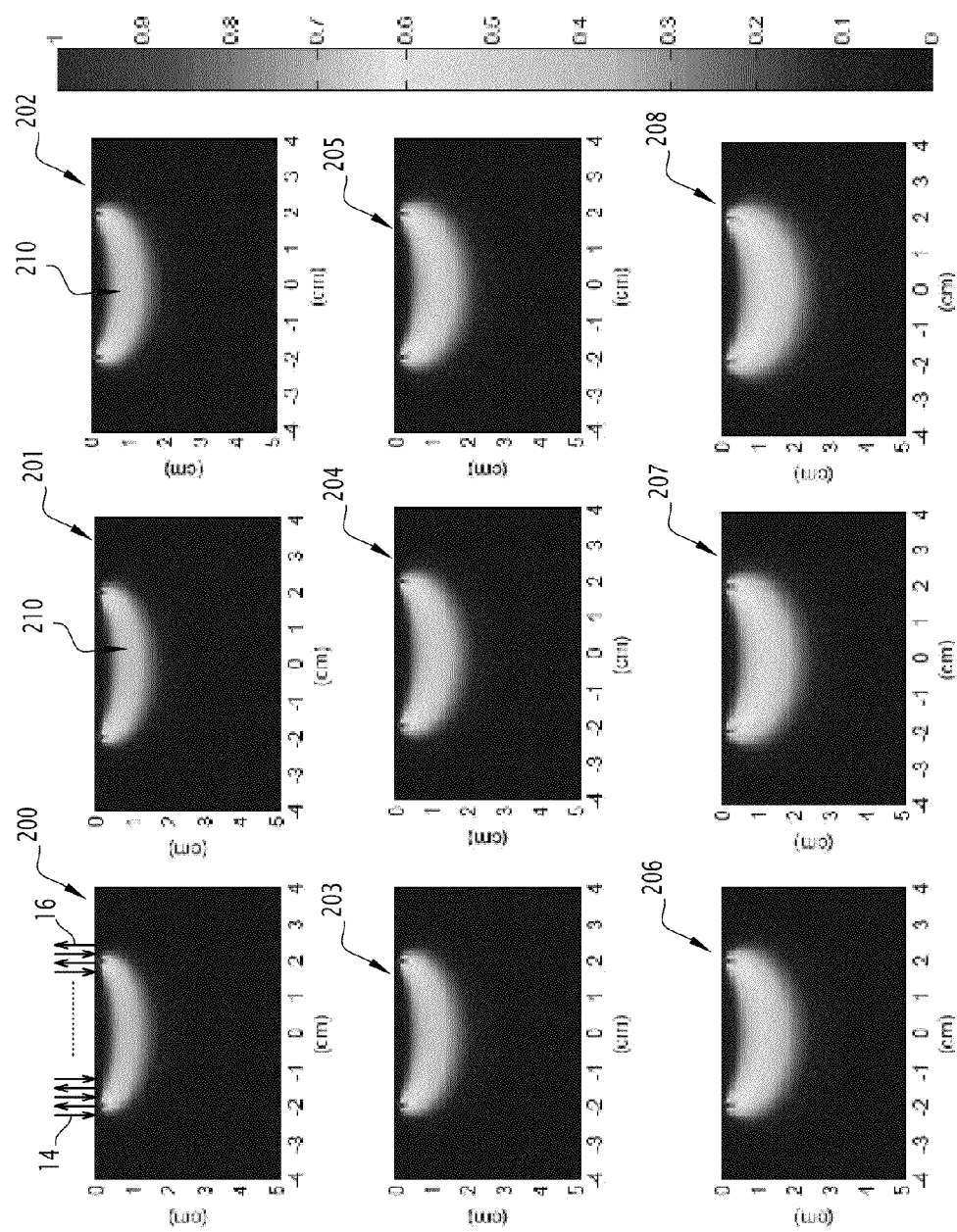
FIG. 4 is a set of images showing sensitivity maps for the computed Mellin-Laplace transforms, each image corresponding to a respective order value and comprised between 0 and 8.

FIG. 4 is a set of images 200 to 208 showing a sensitivity $J_{sd}^{(p,n)}$ defined by the equation:

$$J_{sd}^{(p,n)}(\vec{r}) = \frac{\partial Y_{sd}^{(p,n)}(\vec{r})}{\partial \mu(\vec{r})} \quad (18)$$

for the Mellin-Laplace transforms for all of the corrected time distributions $Y_{sd}^{(p,n)}$, with twenty-one sources 14 and twenty-one detectors 16, respectively symbolized by a down arrow and an up arrow. The space between successive sources 14 and detectors 16 is approximately one millimeter.

Each image 200 to 208 corresponding to a respective increasing value of the order n is between 0 and 8, the image 200 being associated with the order 0 and the image 208 being associated with the order 8. In each image 200 to 208, the set of corrected time distributions $Y_{sd}^{(p,n)}$ corresponds to a banana-shaped light area 210.

One skilled in the art can then note that the higher the value of the order n, the better the sensitivity is in a deep area of the medium 12, for example a depth of more than 1 cm. In other words, the higher the value of the order n, the more the reconstruction system 10 using the method according to the invention can observe the deep area of the medium 12.

Figure 5:
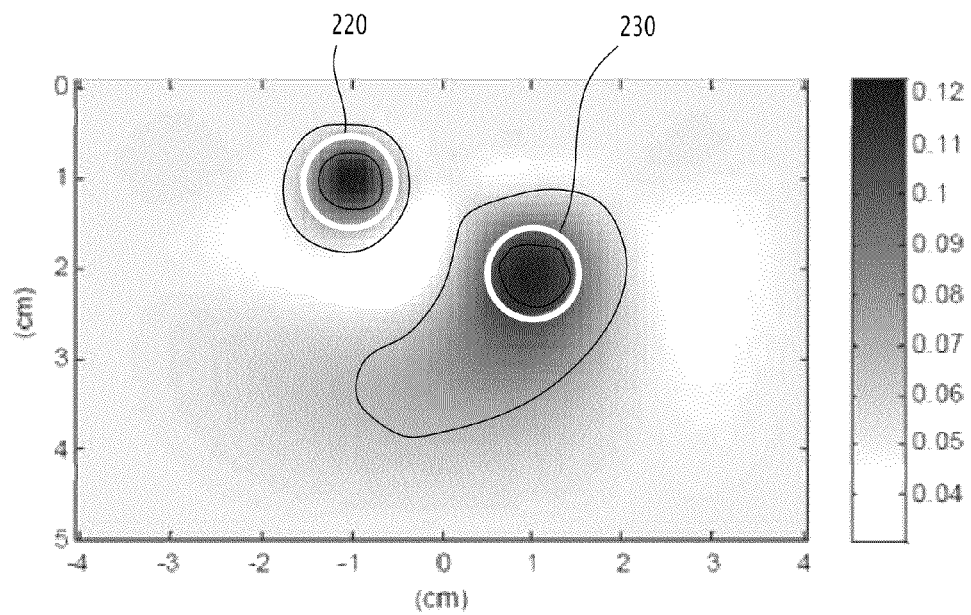
FIG. 5 is a view of an image of the medium reconstructed with a reconstruction system and reconstruction method of the state of the art.
Figure 6:
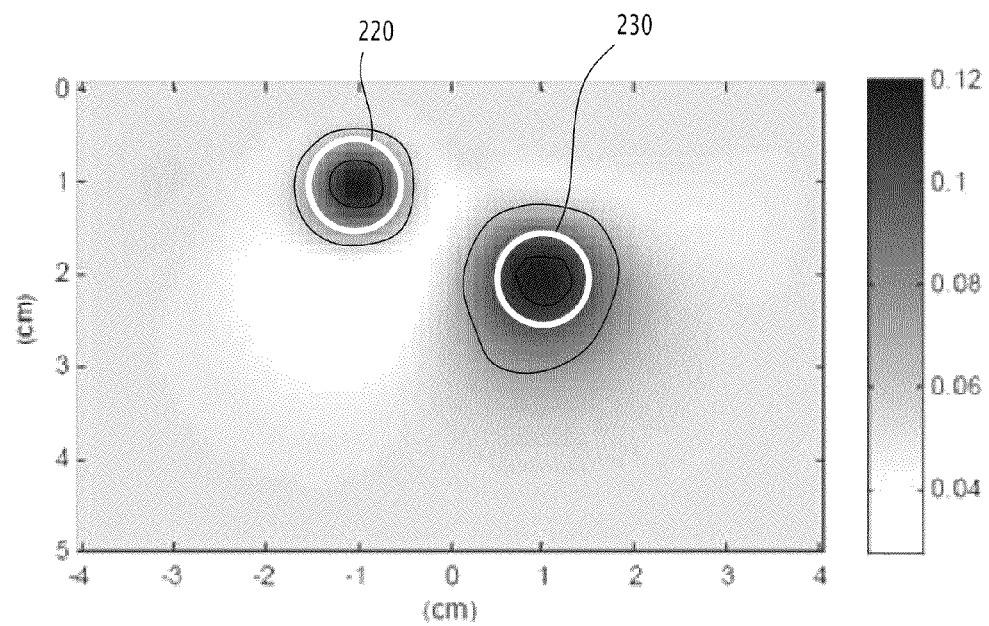
FIG. 6 is a view similar to FIG. 5 with the reconstruction system and reconstruction method according to an example of the invention.

The reconstruction system 10 and the reconstruction method according to examples of the invention allow more precise localization of absorbers positioned deep down than the imaging system and reconstruction method of the state of the art, as shown by FIGS. 5 and 6. FIG. 5 is a view of an image of a medium comprising two absorbers positioned at a depth of 1 cm and 2 cm, respectively, referenced by circles 220 and 230, respectively, reconstructed with an imaging system and a reconstruction method of the state of the art, whereas FIG. 6 is a view of an image of the same medium reconstructed with an imaging system and reconstruction method according to examples of the invention. By comparing FIGS. 5 and 6, one skilled in the art can note that the absorbers are localized more precisely in the case of the imaging system and reconstruction method according to examples of the invention, in particular for the absorber positioned 2 cm deep.

The reconstruction of the optical properties using the combination of a plurality of Mellin-Laplace transforms of the magnitude comprising the processed distribution, in particular using the combination of the $n_{max}+1$ Mellin-Laplace transforms $Y_{sd}^{(p,n)}$, makes it possible to converge toward the solution more quickly, so as to reduce the processing time needed to reconstruct the optical properties of the medium.

Another advantage of such a combination is that it makes it possible to account for the diffused photons detected shortly after the light pulse, i.e. just 1 or 2 ns after the light pulse, also called prompt photons, using a Mellin-Laplace transform with small orders, such as values of the order n between 0 and 5, while also accounting for the so-called delayed photons, i.e. detected several nanoseconds, or even more than 5 ns, after the light pulse. By using Mellin-Laplace transforms of different orders to perform the reconstruction, both the so-called prompt and delayed photons are taken into account, the latter generally coming from greater depths. It is therefore advantageous to perform the reconstruction using input data combining the Mellin-Laplace transforms of different orders. "Input data" refers to the observed data, i.e. the terms making up the observation vector $\underline{Y}$.

We now describe another example according to which the corresponding instrument response $IRF_{sd}(t)$ is determined for each source-detector pair.

The reconstruction is done using an iterative method, by performing a measurement $B_{sd}(t)$ for one or more source-detector pair(s).

For each source-detector pair, the following equation is then obtained:

$$B_{sd}(t)-B_{sd}^1(t)=-S_s(t)*(\int G_s^1(\vec{r},t)*\delta\mu_a(\vec{r},t)* G_d^1(\vec{r},t)d\vec{r}+\int \vec{\nabla} G_s^1(\vec{r},t)*\delta D(\vec{r},t)*\vec{\nabla} G_d^1(\vec{r},t)d\vec{r})*D_d(t) \quad (19)$$

where:

$B_{sd}^1$ represents a modeled measurement considering that the medium has the absorption $\mu_a^1(r)$ and diffusion $D_a^1(r)$ coefficients determined during the previous iteration, the values $\mu_a^1(r)$ and $D_a^1(r)$ being initialized during the first iteration by a first estimate done by the operator, the coefficients $\delta\mu_a(\vec{r},t)$ and $\delta D(\vec{r},t)$ represent the difference between the optical properties of the medium ($\mu_a$, D) and the initial optical properties ($\mu_a^1$, $D^1$), or those resulting from the previous iteration.

Similarly to the previous example, the aim is to minimize $\delta\mu_a(\vec{r},t)$ and $\delta D(\vec{r},t)$.

If $B_{sd}(t)$ is a measurement done on the medium to be characterized MC for a given source-detector pair sd, the Mellin-Laplace transforms are determined of a function $Y_{sd}$, said transforms assuming the form:

$$Y_{s,d}^{(p,n)} = \frac{B_{s,d}^{(p,n)} - \sum_{i=0}^{n-1} IRF_{s,d}^{(p,n-i)} B_{s,d}^{(p,i)}}{I_{s,d}^{(p,0)}} \quad (20)$$

Thus, as a function of the Mellin-Laplace transforms of the instrument response $IRF_{s,d}^{(p,k)}$, with $0 \le k \le n$, and the measurement $B_{s,d}^{(p,k)}$ with $0 \le k \le n$, one determines $Y_{s,d}^{(p,n)}$:

$$Y_{s,d}^{(p,n)} = \left( \int_\Omega \sum_{j+k=n} G_s^{1(p,j)}(\vec{r}) \cdot \delta\mu_a(\vec{r}) \cdot G_d^{1(p,k)}(\vec{r}) \, d\vec{r} + \right.$$

$$\left. \int_\Omega \sum_{j+k=n} G_s^{1(p,j)}(\vec{r}) \cdot \delta D(\vec{r}) \cdot G_d^{1(p,k)}(\vec{r}) \, d\vec{r} \right) \quad (21)$$

After discretization of the medium in M voxels m, this expression becomes:

$$Y_{s,d}^{(p,n)} = \sum_{m=1}^{M} \left( \sum_{j+k=n} G_s^{1(p,j)}(\vec{r}_m) \cdot \delta\mu_a(\vec{r}_m) \cdot G_d^{1(p,k)}(\vec{r}_m) V_m + \sum_{j+k=n} G_s^{1(p,j)}(\vec{r}_m) \cdot \delta D(\vec{r}_m) \cdot G_d^{1(p,k)}(\vec{r}_m) V_m \right) \quad (22)$$

An iterative inversion algorithm is then implemented to define the optical properties minimizing the vectors $\delta\mu_a(\vec{r}_m)$ and $\delta D(\vec{r}_m)$, from a plurality of Mellin-Laplace transforms $Y_{s,d}^{(p,n)}$, with different orders, obtained using measurements done with a plurality of source-detector pairs.

According to a further example, the Mellin-Laplace transform is used to establish a fluorescence map $F(\vec{r})$, with $F(\vec{r}) = \mu_a(\vec{r})\eta$, $\eta$ being the fluorescence output of the fluorophore localized in the volume $d\vec{r}$. A response function of the fluorophore $F(\vec{r},t)$ is defined, such that $$F(\vec{r}, t) = F(\vec{r}) \exp\left(-\frac{t}{\tau}\right) \quad (23)$$

with $\tau$ designating the lifetime of the fluorophore.

Using an excitation source s and a detector d like those defined in the first embodiment, a time measurement $B_{sd}(t)$ is done on the medium to be characterized MC.

This measurement is written:

$$B_{sd}(t) = IRF_{sd}(t) * \int_\Omega G_s(\vec{r},t) * F(\vec{r},t) * G_d(\vec{r},t) \, d\vec{r} \quad (24)$$

where $G_s(\vec{r},t)$ and $G_d(\vec{r},t)$ are Green functions representing the photon density between the source s and the point $\vec{r}$ of the medium, and between the point $\vec{r}$ of the medium and the detector d, respectively.

Since $$\left[ \frac{\exp(-t/\tau)}{\tau} \right]^{(p,n)} = \frac{p^n}{n!} \int_0^\infty t^n \frac{\exp(-t/\tau)}{\tau} \cdot dt = (p\tau)^n \quad (25)$$

we obtain:

$$F^{(p,n)}(\vec{r}) = F(\vec{r})(p\tau)^n \quad (26)$$

The Mellin-Laplace transform of the measured time distribution $B_{sd}$ is therefore:

$$B_{sd}^{(p,n)} = \sum_{i+j+k+l=n} IRF_{sd}^{(p,i)} \cdot (p\tau)^j \cdot \int_\Omega G_s^{(p,k)}(\vec{r}) \cdot F(\vec{r}) \cdot G_{sd}^{(p,l)}(\vec{r}) \, d\vec{r} \quad (27)$$

After discretization of the medium in M voxels m, one obtains:

$$B_{sd}^{(p,n)} = \sum_{i+j+k+l=n} IRF_{sd}^{(p,i)} \cdot (p\tau)^j \sum_{m=1}^{M} \left( G_s^{(p,k)}(\vec{r}_m) \cdot F(\vec{r}_m) \cdot G_{sd}^{(p,l)}(\vec{r}_m) V_m \right) \quad (28)$$

Lastly, the system is inverted after discretization of the medium and voxels. An inversion algorithm is then implemented, such as one of the known algorithms previously mentioned, to define the vector $F(\vec{r}_m)$ corresponding to the desired fluorescence map, from the plurality of Mellin-Laplace transforms $Y_{s,d}^{(p,n)}$, with different orders, obtained using measurements done with a plurality of source-detector pairs sd.

Similarly to the above example, the combination of different Mellin-Laplace transforms with a magnitude $Y_{s,d}^{(p,n)}$ corresponding to a source-detector pair, and in particular the use of different values of the order n, makes it possible to better account for the contributions of the prompt photons and delayed photons, the latter essentially coming from greater depths.

The invention claimed is:

1. A method for reconstructing the optical properties of a medium, using a reconstruction system comprising at least one radiation source capable of lighting the medium and at least one detector capable of receiving a signal transmitted by the medium, the method including the following steps:
    lighting the medium using the radiation source,
    receiving, by the detector, the signal transmitted by the medium, and
    processing, at least one source-detector pair, of a first distribution of the signal received by the detector,
    computing the Mellin-Laplace transform, for a given order and a given variable, of a magnitude comprising the first distribution, the order being an integer, the variable being a real number, and
    reconstructing optical properties of the medium using the Mellin-Laplace transform of said magnitude,
    wherein the computing step comprises computing a plurality of Mellin-Laplace transforms of said magnitude for distinct values of the order, and in that the reconstructing step is carried out from a combination of the plurality of Mellin-Laplace transforms.

2. The method according to claim 1, wherein the computing step comprises the computation of at least one Mellin-Laplace transform of said magnitude for an order value greater than or equal to 5.

3. The method according to claim 2, wherein the computing step comprises the computation of $n_{max}+1$ Mellin-Laplace transforms, the order successively taking all values comprised between 0 and $n_{max}$, $n_{max}$ being greater than or equal to 5.

4. The method according to claim 2, wherein the computing step comprises the computation of $n_{max}+1$ Mellin-Laplace transforms, the order successively taking all values comprised between 0 and $n_{max}$, $n_{max}$ being greater than or equal to 8.

5. The method according to claim 1, wherein the value of the variable is between 1 ns$^{-1}$ and 20 ns$^{-1}$.

6. The method according to claim 1, wherein the method further comprises the step of:
    determining, for at least one source-detector pair, a first modeling function of a diffusion signal of the light between the source and the detector in the medium, processing, for said at least one source-detector pair, a second distribution of a signal received by the detector for a reference medium, the received signal being transmitted by the reference medium following the lighting of said medium by the source, and determining, for at least one source-detector pair, a second modeling function of a diffusion signal of the light between the source and the detector in the reference medium, and wherein said magnitude depends on the first distribution, the first modeling function, the second distribution and the second modeling function.

7. The method according to claim 6, wherein said magnitude is obtained by subtracting the product of the second distribution and the first modeling function from the product of the first distribution and the second modeling function.

8. The method according to claim 6, wherein said magnitude is the ratio between the product of the first distribution and the second modeling function and the product of the second distribution and the first modeling function.

9. The method according to claim 1, wherein the radiation source comprises a pulsed light source.

10. The method according to claim 1, wherein the detector is a time-resolved detector.

11. The method according to claim 1, wherein the optical properties include at least one element from amongst the group consisting of:
  light absorption properties, in particular, the absorption coefficient,
  diffusion properties, in particular, the reduced diffusion coefficient or the diffusion coefficient, and
  fluorescence properties, in particular, a response function of a fluorophore, or by a concentration of the fluorophore, or by a magnitude depending on the quantity of the fluorophore.

12. The method according to claim 1, wherein the computing step comprises the computation of at least one Mellin-Laplace transform of said magnitude for an order value greater than or equal to 8.

13. A system for reconstructing optical properties of a medium, including:
  a radiation source capable of lighting the medium,
  a detector capable of receiving a signal transmitted by the medium,
  a processor processing a distribution of the signal received by the detector for at least one source-detector pair,
  a device computing the Mellin-Laplace transform, for a given order and a given variable,
  of a magnitude comprising the distribution, the order being an integer, the variable being
  a real number, and
  for a reconstructing device reconstructing the optical properties of the medium using the Mellin-Laplace transform of said magnitude,
  wherein the computing device computes the plurality of Mellin-Laplace transforms of said magnitude for distinct values of the order, and in that the reconstruction means are capable of reconstructing the optical properties of the medium from a combination of the plurality of Mellin-Laplace transforms.

14. The system according to claim 13, wherein the computing device computes at least one Mellin-Laplace transform of said magnitude for an order value greater than or equal to 5.

15. The system according to claim 13, wherein the computing device computes at least one Mellin-Laplace transform of said magnitude for an order value greater than or equal to 8.

* * * * *